United States Patent [19]

Matsuda et al.

[11] 4,272,435
[45] Jun. 9, 1981

[54] PROCESS FOR THE PREPARATION OF AZO COMPOUNDS FROM AMINO COMPOUNDS IN THE PRESENCE OF A PHASE TRANSFER CATALYST

[75] Inventors: Teruo Matsuda; Shigeo Wake, both of Niihama; Tetsuya Shiozaki, Saijo, all of Japan

[73] Assignee: Sumitomo Chemical Company, Limited, Osaka, Japan

[21] Appl. No.: 945,504

[22] Filed: Sep. 25, 1978

[30] Foreign Application Priority Data

Oct. 12, 1977 [JP] Japan .................. 52-122725
Dec. 19, 1977 [JP] Japan .................. 52-153363
Apr. 18, 1978 [JP] Japan .................. 53-46351

[51] Int. Cl.$^3$ .................. C07C 107/00; C07C 107/02; C07C 107/04
[52] U.S. Cl. .................. 260/192
[58] Field of Search .................. 260/192

[56] References Cited

U.S. PATENT DOCUMENTS

| | | |
|---|---|---|
| 2,515,628 | 7/1950 | Castle .................. 260/192 |
| 2,711,405 | 6/1955 | Anderson .................. 260/192 |
| 2,713,576 | 7/1955 | Anderson .................. 260/192 |
| 3,775,395 | 11/1973 | Koyanagi et al. .................. 260/192 |
| 3,783,148 | 1/1974 | Fuchs .................. 260/192 |
| 3,937,696 | 2/1976 | Knowles et al. .................. 260/192 |
| 4,028,345 | 6/1977 | Moore .................. 260/192 |
| 4,051,124 | 9/1977 | Moore .................. 260/192 |
| 4,061,590 | 12/1977 | Moore .................. 260/192 X |

FOREIGN PATENT DOCUMENTS

50-148313 11/1975 Japan .................. 260/192
1168406 10/1969 United Kingdom .................. 260/192

OTHER PUBLICATIONS

Weber et al., "Phase Transfer Catalysis in Organic Synthesis", vol. 4, pp. 3 to 7, (1977).

*Primary Examiner*—Floyd D. Higel
*Attorney, Agent, or Firm*—Stevens, Davis, Miller & Mosher

[57] ABSTRACT

Azo compounds of the formula,

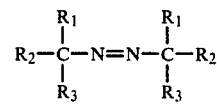

wherein each of $R_1$ and $R_2$ is selected from the group consisting of (1) $C_1$-$C_8$ aliphatic hydrocarbons unsubstituted or substituted with carboxyl, hydroxyl or alkoxy of the formula $-OR_4$ in which $R_4$ is a $C_1$-$C_4$ aliphatic hydrocarbon, (2) $C_3$-$C_8$ alicyclic hydrocarbons, (3) $C_6$-$C_{10}$ aromatic hydrocarbons and (4) $C_4$-$C_{12}$ alicyclic hydrocarbons formed by combining $R_1$ and $R_2$ together with the adjacent carbon atom, and $R_3$ is selected from the group consisting of nitrile, esters of the formula $-COOR_4$ in which $R_4$ is a $C_1$-$C_4$ aliphatic hydrocarbon, a carboxylate of the formula $-COOM$ in which M is an alkali metal or alkaline earth metal, and a carboxylamido, which are useful as foaming agents or radical polymerization initiator, are prepared in a high yield by reacting a corresponding amino compound with a metal hypohalite or with an alkyl hypohalite in the presence of an alkali, using a phase transfer catalyst in a heterogeneous medium comprising water and organic solvent, the phase transfer catalyst being one member selected from the group consisting of organic quaternary ammonium salts, organic quaternary phosphonium salts and macrocyclic polyethers.

18 Claims, No Drawings

PROCESS FOR THE PREPARATION OF AZO COMPOUNDS FROM AMINO COMPOUNDS IN THE PRESENCE OF A PHASE TRANSFER CATALYST

The present invention relates to an improvement in a process for producing azo compounds of the formula (I),

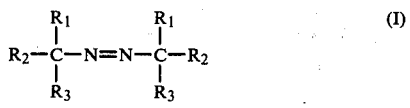

wherein each of $R_1$ and $R_2$ is selected from the group consisting of (1) $C_1$–$C_8$ aliphatic hydrocarbon which may be substituted with carboxyl, hydroxyl or alkoxy of the formula —$OR_4$ in which $R_4$ is $C_1$–$C_4$ aliphatic hydrocarbon, (2) $C_3$–$C_8$ alicyclic hydrocarbon, (3) $C_6$–$C_{10}$ aromatic hydrocarbon and (4) $C_4$–$C_{12}$ alicyclic hydrocarbon formed by combining $R_1$ and $R_2$ together with the adjacent carbon atom, and $R_3$ is selected from the group consisting of nitrile; ester of the formula —$COOR_4$ in which $R_4$ is $C_1$–$C_4$ aliphatic hydrocarbon; carboxylate of the formula —COOM in which M is an alkali metal or alkaline earth metal; and carboxyamido, from an amino compound of the formula (II),

wherein $R_1$, $R_2$ and $R_3$ are as defined above.

The symmetric azo compounds of the above formula (I) have so far been used widely as useful foaming agents or radical polymerization initiators.

The oldest process for producing the azo compounds is described in Annalen der Chemie 290, 1–43 (1896), and this process uses expensive hydrazine as a main raw material. In U.S. Pat. No. 2,515,628, there is disclosed a process which comprises reacting a ketone, sodium cyanide and hydrazine hydrochloride in an aqueous medium and oxidizing the resulting hydrazo compounds into the azo compounds in water or an alcohol. U.S. Pat. No. 2,586,995 discloses a process which comprises producing a ketazine from a ketone and hydrazine hydrate, converting the ketazine into a hydrazo compound by reaction with liquefied hydrogen cyanide and oxidizing the hydrazo compound into the azo compound. The yield of azo compounds by these processes is very poor in general. An improvement in the process with hydrazine is reported in U.S. Pat. No. 3,775,395 in which a hydrazo compound is produced by reacting a ketone, hydrazine and hydrogen cyanide in an aqueous medium in the presence of a surface active agent. In this case, the total yield of the azo compound is good. These processes using hydrazine as a main raw material have been improved in many respects, and at present they are employed as a useful industrial process. But, the largest drawback of these processes is that expensive hydrazine must be used as a raw material.

One of the other processes for producing azo compounds is described in U.S. Pat. No. 2,711,405, and this process comprises reacting a cyanohydrin of an aliphatic ketone and ammonia to produce an aminonitrile, and reacting the aminonitrile with a metal hypochlorite in an aqueous medium, thereby converting the aminonitrile into the azo compound by oxidative coupling. The process in U.S. Pat. No. 2,711,405 is relatively useful for producing azobisisobutyronitrile from acetone cyanohydrin through α-aminoisobutyronitrile. When this process is, however, applied to the aminonitrile of a ketone having a larger molecular weight, the yield of the coupling reaction is extremely poor. U.S. Pat. No. 3,783,148 discloses an improvement of this process in which methanol or ethanol is used as a reaction solvent. But the reaction conditions of this process are limited very strictly as follows: In order to minimize the decomposition of hypochlorite and more easily control the heat load, the aminonitrile and hypochlorite are preferably added simultaneously. The molar ratio of hypochlorite to aminonitrile should be maintained in the range of 1.4 to 1.8 during the entire course of addition, and the temperature should be kept below −5° C. during the addition. Moreover, loss in alcohol is caused by side reactions or owing to other reasons. Accordingly, this process is not useful for commercial production, and it is desired to develop a process having no such drawbacks.

The inventors extensively studied to overcome these drawbacks, and as a result it was found that the azo compounds of the formula (I) can be obtained from the amino compounds of the formula (II) in a high yield and under mild reaction conditions by using as a catalyst at least one member selected from the group consisting of organic quaternary ammoniums, organic quaternary phosphoniums and macrocyclic polyethers in a heterogeneous reaction medium comprising a water phase and an organic phase.

The present invention provides a process for producing azo compounds of the formula (I),

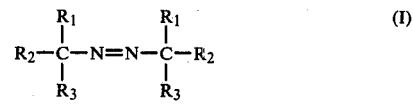

wherein $R_1$, $R_2$ and $R_3$ are as defined above, by reacting an amino compound of the formula (II),

wherein $R_1$, $R_2$ and $R_3$ are as defined above, with a metal hypohalite of the formula (III),

$$M(OX)_n \qquad (III)$$

wherein M is an alkali metal or alkaline earth metal, X is chlorine, bromine or iodine and n is the valence of the metal M, or with an alkyl hypohalite of the formula (IV),

$$R_5OX \qquad (IV)$$

wherein $R_5$ is a $C_1$–$C_6$ aliphatic hydrocarbon group and X is as defined above, in the presence of an alkali, characterized in that said reaction is carried out using as a catalyst at least one member selected from the group consisting of organic quaternary ammonium, organic quaternary phosphoniums and macrocyclic polyethers in a heterogeneous medium comprising water and an organic solvent.

Studies on the use of organic quaternary ammoniums, organic quaternary phosphoniums and macrocyclic polyethers as a phase transfer catalyst have actively been made in recent years, and many reports have been published. There are, however, no reports in which such compounds are applied to the oxidative coupling of the amino compounds of the formula (II).

In carrying out the process of the present invention, the reaction is carried out in a two-phase system comprising a water phase and an organic phase, and in this case, the amounts of water and organic solvent are not particularly limited. But, the amount of water is properly determined of itself, as described hereinafter, from the concentration of metal hypohalite in the water phase and the molar ratio of the metal hypohalite to the amino compound of the formula (II). A suitable amount of the organic solvent is 0.1 to 3 times the weight of water thus determined. Amounts larger than that are not advantageous from an economical viewpoint.

As the organic solvent used in the present invention, there may be used all the solvents which do not react with the metal hypohalites or alkyl hypohalites rapidly and do not form a uniform phase together with the water phase under the reaction conditions of the present invention. But, those having a boiling point higher than 300° C. are disadvantageous since separation of the product from the solvent after completion of the reaction is difficult. As the organic solvent used in the present invention, there may be mentioned, for example, benzene, toluene, xylene, chlorobenzene, benzonitrile, nitrobenzene, hexane, heptane, cyclohexane, cyclopentane, petroleum ether, dichloromethane, chloroform, carbon tetrachloride, 1,2-dichloroethane, 1,1,1-trichloroethane, trichloroethylene, perchloroethylene, methyl formate, ethyl formate, propyl formate, butyl formate, methyl acetate, ethyl acetate, propyl acetate, butyl acetate, methyl propionate, ethyl propionate, methyl butyrate, ethyl butyrate, acetonitrile, propionitrile, butyronitrile, dimethyl ether and diethyl ether. These solvents may be used alone or in combination. Of these, nitriles such as acetonitrile and esters such as ethyl acetate are particularly preferred. Water-soluble solvents may also be used in mixtures with the aforesaid organic solvents, if their amount is such that the water phase and the organic phase do not form a uniform phase under the reaction conditions of the present invention. It sometimes occurs that addition of a small amount of the water-soluble solvent changes the polarity of the water or organic phase, thereby improving the yield. As the water-soluble solvent, there may be mentioned alcohols (e.g. methanol, ethanol, tert-butanol), dimethylformamide (referred to as "DMF" hereinafter), dimethyl sulfoxide (referred to as "DMSO" hereinafter), dioxane, pyridine, mono- or di-alkyl ethers of ethylene glycol (e.g. ethylene glycol dimethyl ether) and the like.

In the process of the present invention, as described hereinbefore, it is essential to carry out the reaction in a heterogeneous solvent system comprising water and an organic solvent which does not form a uniform phase together with the water phase under the reaction conditions of the present invention. As described in the comparative examples which appear hereinafter, the yield is extremely poor when the reaction is carried out in a completely aqueous medium alone.

The process of the present invention can be expressed stoichiometrically by the following chemical equation:

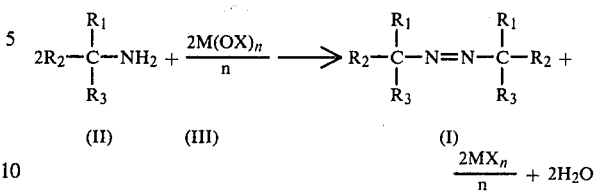

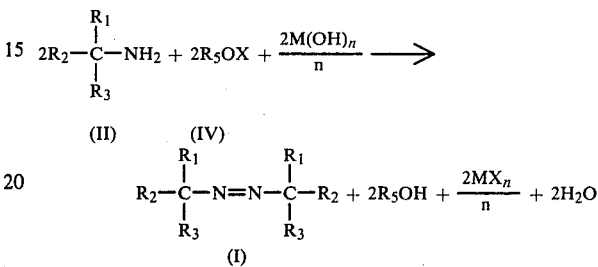

It is believed that this reaction proceeds through chloramine which is an intermediate product.

As examples of $R_1$ and $R_2$ which may be the same or different, there may be mentioned, for example, aliphatic hydrocarbon groups such as methyl, ethyl, propyl, isopropyl, n-butyl, isobutyl, tert-butyl, neopentyl and n-octyl; substituted aliphatic hydrocarbon groups such as 2-carboxyethyl, 4-hydroxybutyl and 2-methyl-2-methoxypropyl; alicyclic hydrocarbon groups such as cyclopropyl and cyclohexyl; aromatic groups such as phenyl, p-chlorophenyl, tolyl and benzyl; and alicyclic hydrocarbon groups formed by combining $R_1$ and $R_2$ together with the adjacent carbon atom such as

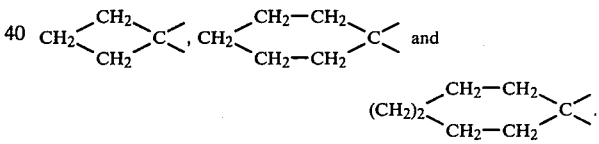

As specific examples of $R_3$, there may be mentioned a nitrile group; ester having as $R_4$ methyl, ethyl, n-propyl, isopropyl, n-butyl or tert-butyl; carboxylate having as M sodium, potassium, or calcium; and carboxyamido such as carboxyamido, N-methylcarboxyamido and dimethylcarboxyamido.

As the metal hypohalites, $M(OX)_n$, used in the process of the present invention, there may be given sodium hypochlorite (NaOCl), potassium hypochlorite (KOCl), calcium hypochlorite [Ca(OCl)$_2$], sodium hypobromite (NaOBr), potassium hypobromite (KOBr), sodium hypoiodite (NaOI) and the like. Of these, sodium hypochlorite is preferred from an economical viewpoint.

As the alkyl hypohalites of the formula, $R_5OX$, there may be used those compounds having a methyl, ethyl, propyl, tert-butyl, tert-amyl group or the like as examples of $R_5$. The alkyl hypohalites are used for the reaction in the presence of an alkali such as sodium hydroxide, potassium hydroxide or calcium hydroxide.

Metal hypohalites, $M(OX)_n$, used in the process of the present invention may be produced by the well-known methods prior to use for reaction, or in situ while adding chlorine, bromine or iodine to the reaction system in the presence of an alkali such as sodium hydroxide or potassium hydroxide. The alkyl hypohalites may also be produced by the well-known methods prior to use for reaction, or in situ while contacting alcohols with metal hypohalites in the reaction system.

In the process of the present invention, it is desirable to carry out the reaction while maintaining the pH of the water phase at 10 to 13. The reaction proceeds even though the pH is outside the above range, but the yield becomes poor in many cases.

In the process of the present invention, the equivalent ratio of the metal hypohalite or alkyl hypohalite to the amino compound of the formula (II) is not critical. When the equivalent ratio is, however, less than 1.0, the yield is not so desirable. The equivalent ratios of more than 2.5 have no merits. In general, the ratio of 1.0 to 2.5 provides a high yield, and the ratio of 1.1 to 1.8 is particularly preferred in terms of yield and economy.

The amino compounds of the formula (II) used as a starting material in the present invention are commercially available or may be produced by the well-known methods. For example, the amino compounds of the formula (II) wherein $R_3$ is a nitrile group, i.e. aminonitriles, can be produced by a method similar to that disclosed in Journal of American Chemical Society 67, 1996 (1945) or U.S. Pat. No. 2,711,405, or by reacting a corresponding ketone with ammonium cyanide. Of the amino compounds of the formula (II), those in which $R_3$ is an ester, carboxylate or carboxyamido can be produced by hydrolysis or esterification of the foregoing aminonitriles.

One of the methods usable for production of the aminonitriles comprises reacting a corresponding ketone with hydrogen cyanide in an amount equimolar to or a small excess to the ketone in the presence of an alkali catalyst such as alkylamines or without any catalyst, and then reacting the resulting reaction product, a ketone cyanohydrin, with ammonia in an amount of 0.9 to 10 times the mole of the ketone. Another method comprises reacting a corresponding ketone with ammonia, followed by reaction with hydrogen cyanide. A further method comprises reacting a corresponding ketone, ammonia and hydrogen cyanide at the same time.

The crude aminonitriles thus obtained generally contain unreacted hydrogen cyanide or ketone, or cyanohydrin in some amounts and large amounts of ammonia and produced water. When these crude aminonitriles containing impurities in large amounts are subjected, as they are, to the oxidative coupling of the present invention, undesirable results are caused in many cases. For example, a large quantity of heat is generated in the coupling reaction; the yield of the product is lowered on account of side reactions; and the use of an excess of metal hypohalite or alkyl hypohalite becomes necessary. For the reasons described above, desirable results are obtained when the impurities-containing crude aminonitriles thus obtained are freed from low-boiling compounds such as ammonia by distillation, and then subjected to the present oxidative coupling. But every aminonitrile is an unstable compound, and particularly it becomes very unstable thermally when it contains impurities such as water, ammonia and hydrogen cyanide. Decomposition of the aminonitrile is promoted by a long-term heating at a high temperature.

The inventors further found the followings: In purification of the crude aminonitriles, when low-boiling compounds containing as the main component ammonia and further hydrogen cyanide, ketones and the like are removed by distillation at 5° to 50° C. (the temperature of a heating portion) under pressure of 400 mmHg or less, aminonitriles having a satisfactory purity can be obtained in a high yield.

The characteristic of the present invention consists in the discovery that aminonitriles are hardly decomposed irrespective of the presence of water in the system when the low-boiling compounds are distilled out of the system at a low temperature of 50° C. or less in a relatively short time. In order to obtain aminonitriles of satisfactory purity under these conditions, it is necessary to distil off the low-boiling compounds at reduced pressure of 400 mmHg or less. When the heating portion containing a crude aminonitrile is heated at a high temperature of 50° C. or more, decomposition of the aminonitrile and other side reactions become violent, which results in lowering of yield and striking coloration of the reaction solution. The low-boiling compounds can be distilled off even at a temperature of 5° C. or less, but temperatures of 5° C. or more are advantageous from the economical standpoint of the temperature of common cooling media. A practical optimum temperature depends upon the kind of aminonitriles and the pressure on distillation, but generally it is preferably 10° to 35° C. When removal of the low-boiling compounds by distillation is carried out at a pressure of 400 mmHg or more, the temperature of the heating portion needs to be raised and the residence time of aminonitrile in the portion is prolonged. As a result, decomposition of the amoninitrile becomes remarkable and the yield is lowered. The lower limit of the pressure is not particularly limited, but pressures of 5 mmHg or more are desirable from the industrial point of view, and particularly it is desirable to carry out distillation within the range of 10 to 150 mmHg. Thus, more desirable results are obtained when the crude aminonitrile is purified by carrying out distillation under the foregoing conditions, thereby removing the low-boiling compounds so that the content of ammonia in the aminonitrile is reduced to 2% by weight or less, and then the purified aminonitriles are subjected to the oxidative coupling of the present invention.

Of the azo compounds of the formula (I) obtained by the process of the present invention, those in which $R_3$ is an ester, carboxylate or carboxyamido can also be obtained by converting aminonitriles of the formula (V),

wherein $R_1$ and $R_2$ are as defined above, into azodinitriles of the formula (VI),

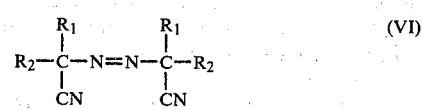

wherein $R_1$ and $R_2$ are as defined above, according to the process of the present invention, followed by hydrolysis or esterification.

It is desirable that the metal hypohalites (III) used in the present invention are in the form of an aqueous solution. Their concentration in the aqueous solution is not particularly limited, but generally concentrations of 5 to 15% by weight are preferred. Dilute aqueous solutions of 5% by weight or less may of course be used, but the amount of water used becomes large. As a result, disadvantages such as an increase in the amount of catalyst (e.g. organic quaternary ammoniums, organic quaternary phosphoniums, macrocyclic polyethers) are required. The amount of the aqueous phase when the alkyl hypohalite (IV) is used is not particularly limited, and it may be less than that in case of the metal hypohalite (III).

In a process wherein the azo compounds of the formula (I) are produced by subjecting the amino compounds of the formula (II) to oxidative coupling using the metal hypohalite (III) or the alkyl hypohalite (IV), the reaction proceeds more smoothly and the yield of the product increases more greatly than expected when at least one member selected from the group consisting of organic quaternary ammoniums, organic quaternary phosphoniums and macrocyclic polyethers is added as a catalyst to the reaction system. In the reaction of the present invention, these catalysts may be considered as probably acting as a phase transfer catalyst or displaying some other functions which enable the reaction of the present invention.

As specific examples of the organic quaternary ammoniums, there may be given chlorides, bromides, iodides, hydroxides, alkoxides or acetoxides of benzyltriethylammonium, benzyltrimethylammonium, benzyltripropylammonium, phenyltrimethylammonium, phenyltriethylammonium, tetrabutylammonium, tetrapropylammonium, tetraethylammonium, tetramethylammonium, triethylpropylammonium, β-hydroxyethyltrimethylammonium, β-bromoethyltrimethylammonium, 3-phenoxybenzyltriethylammonium, ethyltripropylammonium, methyltrioctylammonium, methyltrinonylammonium and the like. Of these, the chlorides, bromides or hydroxides of benzyltriethylammonium and phenyltriethylammonium are preferred.

As specific examples of the organic quaternary phosphoniums, there may be given chlorides, bromides, iodides, hydroxides, alkoxides or acetoxides of triphenylmethylphosphonium, triphenylethylphosphonium, phenyltriethylphosphonium, cethyltributylphosphonium and the like. Of these, a chloride or bromide of triphenylmethylphosphonium is preferred.

As specific examples of the macrocyclic polyethers, there may be given 2,3,11,12-dibenzo-1,4,7,10,13,16-hexaoxacyclooctadecane-2,11-diene(dibenzo-18-Crown-6), 2,3,11,12-dicyclohexyl-1,4,7,10,13,16-hexaoxacyclooctadecane(dicyclohexyl-18-Crown-6), 1,4,7,10,13,16-hexaoxacyclooctadecane(18-Crown-6), 1,4,7,10,13-pentaoxacyclopentadecane(15-Crown-5), 4,7,13,18-tetraoxa-1,10-diazabicyclo(8,5,5)eicosane, 4,7,13,16,21-pentaoxa-1,10-diazabicyclo(8,8,5)tricosane, 4,7,13,16,21,24-hexaoxa-1,10-diazabicyclo(8,8,8)hexacosane, 5,6-benzo-4,7,13,16,21,24-hexaoxa-1,10-diazabicyclo(8,8,8)hexacosane and the like. Of these, dibenzo-18-Crown-6 is preferred.

These catalysts may be used alone or in combination.

The amount of these catalysts, may be varied over a wide range. Even small amounts of about 0.1% by weight based on the weight of the amino compounds (II) may be used. The upper limit of the amount is not critical, and amounts up to 10% by weight provide commercially satisfactory results. Generally, amounts of 0.25 to 5% by weight based on the weight of the amino compounds (II) are particularly preferred in terms of reaction efficiency and economy.

In the process of the present invention, a reaction temperature of 0° to 20° C. is preferred. The reaction temperature may be outside this desirable range and a preferred yield is obtained at −10° to 30° C. When the reaction is carried out at a low temperature of −10° C. or less, there occurs a large danger of the water phase being frozen. In this case, it is possible to carry out the process of the present invention even at −10° C. or less without freezing by using an anti-freezing compound, but the reaction time is prolonged. When the reaction temperature is as high as 30° C. or more, it should be taken into account that various problems such as side reactions, decomposition of the azo compounds (I) reduction of yield occur. That is, the process of the present invention can be carried out at a temperature between the freezing point of the reaction mixture and the decomposition point of the azo compound.

The time required for the reaction to be completed depends upon the reaction temperature and the kind of the amino compounds of the formula (II). It takes 10 minutes to 10 hours for the reaction at the desirable reaction temperature of 0° to 20° C. The reaction time is short when the amino compounds (II) of a relatively low molecular weight are used as the starting material, while it tends to become long when the amino compounds (II) are of a relatively high molecular weight.

The process of the present invention can be carried out in various ways in practice. One of the common methods is to add a solution containing the amino compound of the formula (II) and the aforesaid catalyst to an aqueous metal hypohalite solution with stirring. Another method is to add the aqueous metal hypohalite solution and alcohols separately to the solution containing the amino compound (II) and the catalyst. A further method is to add the reaction components separately to the aqueous catalyst solution. These methods can be applied either batchwise or continuously.

By the process as described hereinbefore, the azo compounds (I) suitable for most usages are obtained in a high yield, but it sometimes occurs that the purity of the azo compounds (I) is not sufficient for some polymerization of vinyl chloride. Further, in synthesis of some low-melting azo compounds by this process, the yield of the azo compounds (I) is sometimes lowered for the reason that crystallization of the compounds is inhibited by some oily compounds which are considered as unreacted materials, intermediates, substances produced by side reactions or mixtures thereof.

In order to solve these problems, the following method is employed: The amino compound of the formula (II) is reacted with the metal hypohalite (III) or the alkyl hypohalite (IV) according to the process of the present invention; and the reaction mixture obtained is then treated with at least one reducing agent selected from the group consisting of nitrites, sulfites, bisulfites, pyrosulfites, thiosulfates, sulfur dioxide, nitrogen oxide, oxalic acid, formaldehyde, hydrazine, hydrogen peroxide and hydroxyamine. Of the reducing agents described above, sodium sulfite, sodium bisulfite and sulfur dioxide are particularly preferred. These reducing agents may be used alone or in combination. Thus, the azo compounds (I) of higher purity are obtained in a high yield.

By applying the aforesaid reduction treatment, surprisingly, the following merits are obtained: Since the foregoing oily impurities are decomposed, crystallization of the azo compounds (I), particularly low-melting ones, becomes easy and thus the azo compounds (I) having a high purity of 98% or more can be obtained in a high yield; consequently, a special purification process for the compounds, for example, recrystallization, can be omitted.

Various methods may be applied for the reduction treatment. For example, one of the methods comprises reacting the amino compound of the formula (II) with the metal hypohalite (III) according to the process of the present invention, adding at least one of the foregoing reducing agents to the resulting reaction mixture comprising a water phase and an organic phase, stirring the mixture for a definite time, and then diluting the organic phase, as it is or after removal of the organic solvent by distillation, with water, thereby isolating the objective azo compound (I). Another method comprises subjecting the amino compound (II) to the oxidative coupling in the same manner as above, separating the water phase from the organic phase after the reaction, adding at least one of the foregoing reducing agents to the organic phase, stirring the mixture for a definite time and then isolating the azo compound (I) from the mixture. A further method comprises subjecting the amino compound (II) to the oxidative coupling, and then diluting the organic phase with a reducing agent-containing water, thereby carrying out precipitation of the azo compound (I) and reduction treatment at the same time. A still further method comprises subjecting the amino compound (II) to the oxidative coupling, removing the solvent from the organic phase by distillation and then adding a reducing agent-containing water to the residue, thereby carrying out precipitation of the azo compound (I) and reduction treatment at the same time. Other methods than those described above may be used, but it is desirable to apply the reduction treatment to the organic phase containing the dissolved azo compound for a definite time.

The amount of reducing agent used is about 1.0 to 3.0 equivalents or more, preferably 1.3 to 3.0 equivalents, per equivalent of oxidative ingredients in the reaction mixture.

The amount of oxidative impurities may be determined by adding the sample of reaction mixture to be treated to an acidified potassium iodide solution and titrating the solution with preferably 0.1 N sodium thiosulfate solution.

In carrying out the reduction treatment of the present invention, the optimum pH depends upon the kind of reducing agents, but it is not particularly limited. Generally, it is desirable to carry out the treatment under an acidic condition. Particularly when inorganic reducing agents are used, the treatment at a pH of 6.5 or less provides more desirable effects in a short treating time. The pH of the reaction mixture to be reduced can be adjusted properly, if necessary, with the ordinary acids such as sulfuric acid or hydrochloric acid. When sulfur dioxide or sodium bisulfite is used as a reducing agent, the compound itself acts also as an acidifying agent. The temperature at which the reduction treatment is carried out is not particularly limited, but generally it is 0° to 30° C. The time required for reduction treatment depends upon the kind of reducing agents and the treating method, and it is not particularly limited. Generally, however, the treatment is finished within 2 hours. Under desirable treating conditions, the treatment is sometimes finished within several minutes.

As described above, by treating the reaction mixture with the reducing agent after the preparation of the azo compounds (I) it is possible to decompose oxidative impurities and facilitate crystallization of the azo compound (I), thereby improving the separating yield and purity of the azo compounds (I).

According to the present invention, as described above, commercial production of various high-purity azo compounds becomes possible, and besides it can be achieved with ease, in a high yield, under mild reaction conditions and yet without using expensive hydrazine as raw material unlike the conventional processes.

The present invention will be illustrated in more detail with reference to the following Examples and Comparative Examples, which are not, however, interpreted as limiting the invention thereto.

In the Examples, all percentages are by weight unless otherwise stated.

EXAMPLE 1

To a 1-liter autoclave were added 7 moles of ammonia and then 3.5 moles of 90%-pure 2-hydroxy-2,4-dimethylpentanonitrile, and the mixture was reacted at 27° C. for 10 hours at a rate of 300 r.p.m. Thus, 2-amino-2,4-dimethylpentanonitrile was synthesized. After reaction, the reaction mixture was taken out of the autoclave, and 44 g of the water phase was separated. The residue was distilled in a wetted wall tower under the following conditions: Temperature of the heating portion 25° C.; pressure 30 mmHg; and residence time in the heating portion 1 minute or less. Low-boiling compounds were thus distilled off and purified 2-amino-2,4-dimethylpentanonitrile was withdrawn from the bottom. The yield of the purified product was 90.0 mole % based on cyanohydrin. This purified product contained 0.5% by weight of ammonia and 0.8% by weight of hydrogen cyanide, and its purity was 90%.

Next, 213 g of a 10% aqueous sodium hypochlorite solution was cooled to 5° C. and 0.5 g of benzyltriethylammonium chloride was added thereto. To the resulting aqueous solution was added 200 ml of an ethyl acetate solution containing 33 g of the resulting 90%-pure 2-amino-2,4-dimethylpentanonitrile over 30 minutes with stirring. This reaction mixture was stirred at 5° to 10° C. for 3 hours, and the organic and water phases were separated from each other. Ethyl acetate was removed from the organic phase under reduced pressure. The resulting white crystals were washed with water and dried to obtain 24.8 g of 2,2'-azobis(2,4-dimethylpentanonitrile). Yield was 85 mole %.

COMPARATIVE EXAMPLE 1

To 213 g (0.286 mole) of a 10% aqueous sodium hypochlorite solution which had been cooled to 5° C. were added 200 ml of an ethyl acetate solution containing 33 g (0.236 mole) of the same 90%-pure 2-amino-2,4-dimethylpentanonitrile as in Example 1 over 30 minutes with stirring. The resulting mixture was stirred at 5° to 10° C. for 6 hours, and the organic and water phases were separated from each other. Ethyl acetate was removed from the organic phase under reduced pressure, but an oily substance alone was obtained and crystals could not be isolated.

COMPARATIVE EXAMPLE 2

To 213 g of a 10% aqueous sodium hypochlorite solution which had been cooled to 5° C. was added 0.5 g of benzyltriethylammonium chloride. To the resulting aqueous solution was added 33 g of the 90%-pure 2-amino-2,4-dimethylpentanonitrile obtained by the aminonitrile synthesis in Example 1 over 30 minutes with stirring. The resulting reaction mixture was stirred at 5° to 10° C. for 4 hours, but an oil substance alone was deposited and crystals could not be isolated.

EXAMPLE 2

In the same manner as in Example 1, 2-amino-2,4-dimethylpentanonitrile and sodium hypochlorite were reacted. By iodometry, it was found that the total oxidative compounds in both the water and ethyl acetate phases after reaction was 0.05 equivalent. The reaction mixture was adjusted to a pH of 6 with a dilute sulfuric acid, and a solution of 6.5 g (0.125 equivalent) of sodium bisulfite in 30 ml of water was added thereto. The resulting mixture was stirred at 15° C. for 30 minutes to effect the reduction. Thereafter, the ethyl acetate phase was separated from the water phase, and the ethyl acetate in the organic phase was removed by distillation. Water was added to the residue and precipitated white crystals were filtered, washed with water and dried to obtain 26.0 g of 2,2'-azobis(2,4-dimethylvaleronitrile). Yield was 89 mole %. The product was analyzed by iodometry, and it was found that the amount of oxidative impurities was 100 ppm or less and that the purity of the product was 99.5%.

EXAMPLE 3

To a 1-liter autoclave were added 121 g of ammonia and then 434 g of 92.0%-pure acetone cyanohydrin, and the mixture was reacted at 25° C. for 4 hours while stirring at a rate of 300 r.p.m. Thus, 2-amino-2-methylpropionitrile was synthesized. The reaction solution was taken out of the autoclave, and distilled in a wetted wall tower under the following conditions: Temperature of the heating portion 25° C.; pressure 30 mmHg; and residence time of the reaction mixture in the heating portion 1 minute or less. Low-boiling compounds were thus distilled off to obtain purified 2-amino-2-methylpropionitrile. The yield of the purified product was 93.0 mole % based on acetone cyanohydrin. The purified 2-amino-2-methylpropionitrile contained 0.40% by weight of ammonia, 0.80% by weight of hydrogen cyanide and 1.2% by weight of acetone.

Next, 266 g (0.286 mole) of a 8% aqueous sodium hypochlorite solution (pH 12) was cooled to 5° C., and to the aqueous solution was added 150 ml of an acetonitrile solution containing 17.7 g (0.2 mole) of the resulting 95%-pure 2-amino-2-methylpropionitrile and 0.6 g of tetrabutylammonium bromide over 30 minutes with stirring. The resulting reaction mixture was stirred at 7° to 10° C. for 30 minutes to complete the reaction. By iodometry, it was found that the total oxidative compounds in both the water and acetonitrile phases after reaction was 0.08 equivalent. This reaction mixture was adjusted to a pH of 6 with a dilute hydrochloric acid and 4.2 g (0.12 equivalent) of sodium nitrite was added thereto, followed by stirring at 15° C. for 20 minutes. Thereafter, the reaction mixture was diluted with 1050 g of water, and the thus precipitated white crystals were filtered, washed with water and dried to obtain 16 g of 2,2'-azobis(isobutyronitrile). The resulting white crystals had a melting point of 104°–105.5° C. and a purity of 99% or more.

EXAMPLES 4 TO 7

Oxidation was carried out in the same manner as in Example 3, except that the equivalent amounts of various amino compounds shown in Table 1 were used in place of the amino compound. Thus, corresponding azo compounds were obtained in a high yield. The results are shown in Table 1.

TABLE 1

| Example | Amino compound | Azo compound | Yield (mole %) |
|---|---|---|---|
| 4 | 2-Amino-4-methoxy-2,4-dimethyl-pentanonitrile | 2,2'-Azobis(4-methoxy-2,4-dimethylpentano-nitrile) | 71.0 |
| 5 | Ethyl 2-amino-2-methylpropionate | Diethyl 2,2'-azo-bis(2-methyl-propionate) | 75.0 |
| 6 | 1-Amino-1-cyano-cyclooctane | 1,1-Azobis(cyclo-octanecarbonitrile) | 78.0 |
| 7 | 2-Amino-2-phenyl-propionitrile | 2,2'-azobis(2-phenylpropio-nitrile) | 80.0 |

EXAMPLE 8

Reaction was carried out in the same manner as in Example 1, except that the equivalent amount of potassium hypobromite was used in place of the sodium hypochlorite. Thus, 2,2'-azobis(2,4-dimethylpentanonitrile) was obtained in yield of 90%.

EXAMPLE 9

A mixture of 200 g of a 13% aqueous sodium hypochlorite solution and 75 ml of acetonitrile was cooled to 5° C. and 0.9 g of phenyltriethylammonium chloride was added thereto. While stirring the mixture at a rate of 400 r.p.m., 75 ml of an acetonitrile solution containing 38.5 g of 2-amino-4-methoxy-2,4-dimethylpentanonitrile (purity 85%; ammonia content 0.2%) was added thereto over 20 minutes. The resulting reaction mixture was stirred at 5° to 10° C. for 5 hours, and then 10 g (0.31 equivalent) of sulfur dioxide gas was added thereto, followed by stirring for 10 minutes. The acetonitrile phase was separated from the water phase, and the solvent in the acetonitrile phase was removed under reduced pressure. The thus precipitated crystals were washed with 200 g of water, filtered and dried. The resulting 2,2'-azobis(2,4-dimethyl-4-methoxyvaleronitrile) had a melting point of 50° to 65° C. The purity of the product was 99% or more. Yield was 72 mole %.

EXAMPLES 10 TO 15

Reaction was carried out in the same manner as in Example 1, except that the catalysts and their amounts shown in Table 2 were used in place of the benzyltriethylammonium chloride. Thus, 2,2'-azobis(2,4-dimethylpentanonitrile) was obtained in a high yield. The results are shown in Table 2.

TABLE 2

| Example | Catalyst | Amount of catalyst based on aminonitrile (weight %) | Yield (mole %) |
|---|---|---|---|
| 10 | Tetrabutylammonium bromide | 3 | 81.0 |

TABLE 2-continued

| Example | Catalyst | Amount of catalyst based on aminonitrile (weight %) | Yield (mole %) |
|---|---|---|---|
| 11 | Phenyltriethyl ammonium chloride | 4 | 88.0 |
| 12 | Methyltricaprylammonium bromide | 2 | 78.0 |
| 13 | Cetyltributylphosphonium bromide | 1 | 87.0 |
| 14 | Dicyclohexyl-18-Crown-6 | 0.5 | 92.0 |
| 15 | 50/50 (by weight) Mixture of the catalysts in Examples 10 and 11 | 3 | 85.0 |

EXAMPLES 16 TO 20

Reaction was carried out in the same manner as in Example 2, except that the solvents shown in Table 3 were used in place of the ethyl acetate. Thus, 2,2'-azobis(2,4-dimethylpentanonitrile) was obtained in a high purity and in an allowable yield. The results are shown in Table 3.

TABLE 3

| Example | Organic solvent | Amount of organic solvent (ml) | Yield (mole %) |
|---|---|---|---|
| 16 | Methyl acetate | 100 | 85.0 |
| 17 | Benzene | 150 | 74.0 |
| 18 | Methylene chloride | 300 | 75.0 |
| 19 | Acetonitrile | 100 | 93.0 |
| 20 | 20:1 Mixed solvent of diethyl ether and DMSO | 150 | 71.0 |

EXAMPLE 21

A mixture of 150 g of ethyl acetate, 23 g of tert-butyl alcohol and 0.5 g of phenyltriethylammonium chloride was cooled to 0° C. While rapidly stirring the mixture, 39.2 g of 85%-pure 2-amino-4-methoxy-2,4-dimethylpentanonitrile and 180 g of a 12.5% aqueous sodium hypochlorite solution were added thereto at separate feed inlets at the same time. The rate of addition of both compounds was controlled so as to finish in 1 hour. The reaction mixture was stirred at 0° to 3° C. for 30 minutes and then at 5° to 10° C. for a further 2 hours.

After the reaction was completed, the organic phase was separated from the water phase, and the solvent in the organic phase was removed under reduced pressure. The resulting crystals were washed with water and dried to obtain 2,2'-azobis(4-methoxy-2,4-dimethylpentanonitrile). Yield was 89 mole %.

What is claimed is:

1. A process for producing an azo compound of the formula (I),

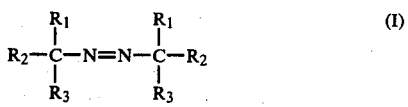

wherein each of $R_1$ and $R_2$ is selected from the group consisting of (1) $C_1$–$C_8$ aliphatic hydrocarbon unsubstituted or substituted with carboxyl, hydroxyl or alkoxy of the formula —$OR_4$ in which $R_4$ is $C_1$–$C_4$ aliphatic hydrocarbon, (2) $C_3$–$C_8$ alicyclic hydrocarbon, (3) $C_6$–$C_{10}$ aromatic hydrocarbon and (4) $C_4$–$C_{12}$ alicyclic hydrocarbon formed by combining $R_1$ and $R_2$ together with the adjacent carbon atom, and $R_3$ is selected from the group consisting of nitrile, ester of the formula —$COOR_4$ in which $R_4$ is $C_1$–$C_4$ aliphatic hydrocarbon, carboxylate of the formula —COOM in which M is an alkali metal or alkaline earth metal, and carboxyamido, by reacting an amino compound of the formula (II), having an ammonia content of 2.0% by weight or less,

wherein $R_1$, $R_2$ and $R_3$ are as defined above, with a metal hypohalide of the formula (III),

wherein M is an alkali metal or alkaline earth metal, X is chlorine, bromine or iodine and n is the valence of the metal M, or with an alkyl hypohalite of the formula (IV),

wherein $R_5$ is $C_1$–$C_6$ aliphatic hydrocarbon and X is as defined above, in the presence of an alkali, characterized in that said reaction is carried out using as a phase transfer catalyst at least one member selected from the group consisting of organic quaternary ammoniums, organic quaternary phosphoniums and macrocyclic polyethers in a heterogeneous medium comprising water and at least one organic solvent selected from the group consisting of nitriles and esters.

2. A process according to claim 1, wherein the equivalent ratio of said metal hypohalite (III) or alkyl hypohalite (IV) to said amino compound (II) is 1.0 to 2.5.

3. A process according to claim 1, wherein said metal hypohalite is sodium hypochlorite.

4. A process according to claim 1, wherein the reaction is carried out at a temperature of 0° to 20° C.

5. A process according to claim 1, wherein the organic quaternary ammonium is a chloride, bromide, iodide, hydroxide, alkoxide or acetoxide of benzyltriethylammonium, benzyltrimethylammonium, benzyltripropylammonium, phenyltrimethylammonium, phenyltriethylammonium, tetrabutylammonium, tetrapropylammonium, tetraethylammonium, tetramethylammonium, triethylpropylammonium, β-hydroxyethyltrimethylammonium, β-bromoethyltrimethylammonium, 3-phenoxybenzyltriethylammonium, ethyltripropylammonium, methyltrioctylammonium or methyltrinonylammonium.

6. A process according to claim 1, wherein the organic quaternary phosphonium is a chloride, bromide, iodide, hydroxide, alkoxide or acetoxide of triphenylmethylphosphonium, triphenylethylphosphonium, phenyltriethylphosphonium, or cetyltributylphosphonium.

7. A process according to claim 1, wherein the macrocyclic polyether is 2,3,11,12-dibenzo-1,4,7,10,13,16-hexaoxacyclooctadecane-2,11-diene(dibenzo-18-Crown-6), 2,3,11,12-dicyclohexyl-1,4,7,10,13,16-hexaoxacyclooctadecane(dicyclohexyl-18-Crown-6), 1,4,7,10,13,16-hexaoxacyclooctadecane(18-Crown-6), 1,4,7,10,13-pentaoxacyclopentadecane(15-Crown-5), 4,7,13,18-tetraoxa-1,10-diazabicyclo(8,5,5)eicosane, 4,7,13,16,21-pentaoxa-1,10-diazabicyclo(8,8,5)tricosane, 4,7,13,16,21,24-hexaoxa-1,10-diazabicyclo(8,8,8)hexacosane or 5,6-benzo-4,7,13,16,21,24-hexaoxa-1,10-diazabicyclo(8,8,8)hexacosane.

8. A process according to claim 1, wherein the organic solvent is selected from the group consisting of methyl formate, ethyl formate, propyl formate, butyl formate, methyl acetate, ethyl acetate, propyl acetate, butyl acetate, methyl propionate, ethyl propionate, methyl butyrate, ethyl butyrate, acetonitrile, propionitrile, butyronitrile and benzonitrile.

9. A process according to claim 1, wherein the catalyst is used in an amount of 0.1 to 10% by weight based on the weight of the amino compound (II).

10. A process according to claim 1, wherein the metal hypohalite is used in the form of an aqueous solution having a concentration of 5 to 15% by weight.

11. A process according to claim 1, wherein the organic solvent is used in an amount of 0.1 to 3 times the weight of water.

12. A process according to claim 1, wherein, after the reaction is finished, the reaction mixture is treated with at least one reducing agent selected from the group consisting of nitrites, sulfites, bisulfites, pyrosulfites, thiosulfates, sulfur dioxide, nitrogen oxide, oxalic acid, formaldehyde, hydrazine, hydrogen peroxide and hydroxylamine.

13. A process according to claim 12, wherein said reducing agent is sodium bisulfite.

14. A process according to claim 1, wherein the amino compound (II) is an α-aminonitrile compound.

15. A process according to claim 14, wherein the α-aminonitrile compound is produced by reacting
 (a) a corresponding ketone and ammonium cyanide,
 (b) a corresponding ketone, ammonium and hydrogen cyanide, or
 (c) ammonia and a cyanohydrin obtained by reacting a corresponding ketone and hydrogen cyanide, to obtain a crude aminonitrile and then distilling the crude aminonitrile at a pressure of 400 mmHg or less and at a still temperature of 5° to 50° C., thereby distilling off low-boiling compounds.

16. A process according to claim 14, wherein the α-aminonitrile is 2-amino-2,4-dimethylpentanonitrile or 2-amino-2,4-dimethyl-4-methoxypentanonitrile.

17. A process for producing an azo compound of the formula (I),

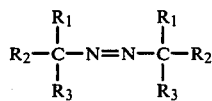
(I)

wherein each of $R_1$ and $R_2$ is selected from the group consisting of (1) $C_1-C_8$ aliphatic hydrocarbon unsubstituted or substituted with carboxyl, hydroxyl or alkoxy of the formula $—OR_4$ in which $R_4$ is $C_1-C_4$ aliphatic hydrocarbon, (2) $C_3-C_8$ alicyclic hydrocarbon, (3) $C_6-C_{10}$ aromatic hydrocarbon and (4) $C_4-C_{12}$ alicyclic hydrocarbon formed by combining $R_1$ and $R_2$ together with the adjacent carbon atom, and $R_3$ is selected from the group consisting of nitrile, ester of the formula $—COOR_4$ in which $R_4$ is $C_1-C_4$ aliphatic hydrocarbon, carboxylate of the formula $—COOM$ in which M is an alkali metal or alkaline earth metal, and carboxyamido, by reacting an amino compound of the formula (II), having an ammonia content of 2.0% by weight or less,

(II)

wherein $R_1$, $R_2$ and $R_3$ are as defined above, with a metal hypohalite of the formula (III),

(III)

wherein M is an alkali metal or alkaline earth metal, X is chlorine, bromine or iodine and n is the valence of the metal M, or with an alkyl hypohalite of the formula (IV),

(IV)

wherein $R_5$ is $C_1-C_6$ aliphatic hydrocarbon and X is as defined above, in the presence of an alkali, characterized in that said reaction is carried out using as a phase transfer catalyst at least one member selected from the group consisting of (a) a chloride, bromide, iodide, hydroxide, alkoxide or acetoxide of organic quaternary ammoniums, (b) a chloride, bromide, iodide, hydroxide, alkoxide or acetoxide or organic quaternary phosphoniums, and (c) a macrocyclic polyether selected from the group consisting of 2,3,11,12-dibenzo-1,4,7,10,13,16-hexaoxacyclooctadecane-2,11-diene(dibenzo-18-Crown-6), 2,3,11,12-dicyclohexyl-1,4,7,10,13,16-hexaoxacyclooctadecane-(dicyclohexyl-18-Crown-6), 1,4,7,10,13,16-hexaoxacyclooctadecane(18-Crown-6), 1,4,7,10,13-pentaoxacyclopentadecane-(15-Crown-5), 4,7,13,18-tetraoxa-1,10-diazabicyclo(8,5,5)-eicosane, 4,7,13,16,21-pentaoxa-1,10-diazabicyclo(8,8,5)-tricosane, 4,7,13,16,21,24-hexaoxa-1,10-diazabicyclo(8,8,8)-hexacosane or 5,6-benzo-4,7,13,16,21,24-hexaoxa-1,10-diazabicyclo(8,8,8)hexacosane in a heterogeneous medium comprising water and at least one organic solvent selected from the group consisting of nitriles and esters.

18. The process according to claim 12, wherein said reducing agent is sodium sulfite, sodium bisulfite or sulfur dioxide.

* * * * *

REEXAMINATION CERTIFICATE (298th)

United States Patent [19]

Matsuda et al.

[11] B1 4,272,435

[45] Certificate Issued Jan. 15, 1985

[54] PROCESS FOR THE PREPARATION OF AZO COMPOUNDS FROM AMINO COMPOUNDS IN THE PRESENCE OF A PHASE TRANSFER CATALYST

[75] Inventors: Teruo Matsuda; Shigeo Wake, both of Niihama; Tetsuya Shiozaki, Saijo, all of Japan

[73] Assignee: Sumitomo Chemical Company, Limited, Osaka, Japan

Reexamination Request:
No. 90/000,337, Mar. 7, 1983

Reexamination Certificate for:
Patent No.: 4,272,435
Issued: Jun. 9, 1981
Appl. No.: 945,504
Filed: Sep. 25, 1978

[30] Foreign Application Priority Data

Oct. 12, 1977 [JP] Japan ................ 52-122725
Dec. 19, 1977 [JP] Japan ................ 52-153363
Apr. 18, 1978 [JP] Japan ................ 53-46351

[51] Int. Cl.³ .............. C07C 107/00; C07C 107/02; C07C 107/04
[52] U.S. Cl. .............................................. 260/192
[58] Field of Search ..................................... 260/192

[56] References Cited

U.S. PATENT DOCUMENTS 3,541,132 11/1970 Knowles ............ 260/465.5
3,937,696 2/1976 Knowles et al. ......... 260/192
4,028,345 6/1977 Moore ................ 260/192
4,051,124 9/1977 Moore ................ 260/192
4,061,590 12/1977 Moore ................ 252/426

OTHER PUBLICATIONS

Weber et al., "Phase Transfer Catalysis in Organic Synthesis", vol. 4, pp. 13-14, (1977).

*Primary Examiner*—Thomas A. Waltz

[57] ABSTRACT

Azo compounds of the formula,

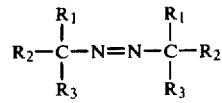

wherein each of $R_1$ and $R_2$ is selected from the group consisting of (1) $C_1$-$C_8$ aliphatic hydrocarbons unsubstituted or substituted with carboxyl, hydroxyl or alkoxy of the formula —$OR_4$ in which $R_4$ is a $C_1$-$C_4$ aliphatic hydrocarbon, (2) $C_3$-$C_8$ alicyclic hydrocarbons, (3) $C_6$-$C_{10}$ aromatic hydrocarbons and (4) $C_4$-$C_{12}$ alicyclic hydrocarbons formed by combining $R_1$ and $R_2$ together with the adjacent carbon atom, and $R_3$ is selected from the group consisting of nitrile, esters of the formula —$COOR_4$ in which $R_4$ is a $C_1$-$C_4$ aliphatic hydrocarbon, a carboxylate of the formula —COOM in which M is an alkali metal or alkaline earth metal, and a carboxylamido, which are useful as foaming agents or radical polymerization initiator, are prepared in a high yield by reacting a corresponding amino compound with a metal hypohalite or with an alkyl hypohalite in the presence of an alkali, using a phase transfer catalyst in a heterogeneous medium comprising water and organic solvent, the phase transfer catalyst being one member selected from the group consisting of organic quaternary ammonium salts, organic quaternary phosphonium salts and macrocyclic polyethers.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 17 is confirmed.

Claims 1, 6, and 7 are determined to be patentable as amended.

Claims 2–5, 8–16 and 18, dependent on an amended claim, are determined to be patentable.

New claims 19 and 20 are added and determined to be patentable.

1. A process for producing an azo compound of the formula (I),

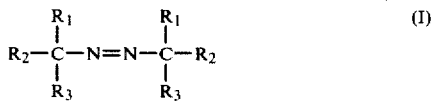

wherein each of $R_1$ and $R_2$ is selected from the group consisting of (1) $C_1$–$C_8$ aliphatic hydrocarbon unsubstituted or substituted with carboxyl, hydroxyl or alkoxy of the formula —$OR_4$ in which $R_4$ is $C_1$–$C_4$ aliphatic hydrocarbon, (2) $C_3$–$C_8$ alicyclic hydrocarbon, (3) $C_6$–$C_{10}$ aromatic hydrocarbon and (4) $C_4$–$C_{12}$ alicyclic hydrocarbon formed by combining $R_1$ and $R_2$ together with the adjacent carbon atom, and $R_3$ is selected from the group consisting of nitrile, ester of the formula —$COOR_4$ in which $R_4$ is $C_1$–$C_4$ aliphatic hydrocarbon, carboxylate of the formula —COOM in which M is an alkali metal or alkaline earth metal, and carboxyamido, by reacting an amino compound of the formula (II), having an ammonia content of 2.0% by weight or less,

wherein $R_1$, $R_2$ and $R_3$ are as defined above, with a metal *hypohalite* [hypohalide] of the formula (III),

wherein M is an alkali metal or alkaline earth metal, X is chlorine, bromine or iodine and n is the valence of the metal M, or with an alkyl hypohalite of the formula (IV),

wherein $R_5$ is $C_1$–$C_6$ aliphatic hydrocarbon and X is as defined above, in the presence of an alkali, characterized in that said reaction is carried out using as a phase transfer catalyst at least one member selected from the group consisting of organic quaternary ammoniums, organic quaternary phosphoniums and macrocyclic polyethers in a heterogeneous medium comprising water and at least one organic solvent selected from the group consisting of nitriles and esters.

6. A process according to claim 1, wherein the *phase transfer catalyst is an* organic quaternary phosphonium *which* is a chloride, bromide, iodide, hydroxide, alkoxide or acetoxide of triphenylmethylphosphonium, triphenylethylphosphonium, phenyltriethylphosphonium, or cetyltributylphosphonium.

7. A process according to claim 1, wherein the *phase transfer catalyst is a* macrocyclic polyether *which* is 2,3,11,12-dibenzo-1,4,7,10,13,16-hexaoxacyclooctadecane-2,11-diene(diebenzo-18-Crown-6), 2,3,11,12-dicyclohexyl-1,4,7,10,13,16-hexaoxacyclooctadecane(dicyclohexyl-18-Crown-6), 1,4,7,10,13,16-hexaoxacyclooctadecane(18-Crown-6), 1,4,7,10,13-pentaoxacyclopentadecane(15-Crown-5), 4,7,13,18-tetraoxa-1,10-diazabicyclo(8,5,5)eicosane, 4,7,13,16,21-pentaoxa-1,10-diazabicyclo(8,8,5)tricosane, 4,7,13,16,21,24-hexaoxa-1,10-diazabicyclo(8,8,8)hexacosane or 5,6-benzo-4,7,13,16,21,24-hexaoxa-1,10-diazabicyclo(8,8,8)hexacosane.

*19. The process according to claim 1 wherein the organic solvent is an ester.*

*20. The process according to claim 1 wherein the organic solvent is a nitrile.*

* * * * *